United States Patent
Schepis et al.

(10) Patent No.: US 11,903,633 B2
(45) Date of Patent: Feb. 20, 2024

(54) RADIOFREQUENCY PROBE, SYSTEM, AND METHOD FOR ADAPTIVE MULTIVARIATE CONTROL OF AN ABLATION PROCEDURE

(71) Applicant: Avent, Inc., Alpharetta, GA (US)

(72) Inventors: Eric A. Schepis, Alpharetta, GA (US); Ryan B. Caldwell, Alpharetta, GA (US); Jalpa S. Shah, Cumming, GA (US); Lee C. Burnes, Canton, GA (US); Amol Soin, Dayton, OH (US)

(73) Assignee: Avent, Inc., Alpharetta, GA (US)

( * ) Notice: Subject to any disclaimer, the term of this patent is extended or adjusted under 35 U.S.C. 154(b) by 207 days.

(21) Appl. No.: 17/137,810

(22) Filed: Dec. 30, 2020

(65) Prior Publication Data
US 2022/0202471 A1 Jun. 30, 2022

(51) Int. Cl.
*A61B 18/14* (2006.01)
*A61B 18/00* (2006.01)
*A61B 18/16* (2006.01)

(52) U.S. Cl.
CPC .............. *A61B 18/14* (2013.01); *A61B 18/16* (2013.01); *A61B 2018/00023* (2013.01);
(Continued)

(58) Field of Classification Search
CPC .......... A61B 18/14; A61B 2018/00023; A61B 2018/00065; A61B 2018/00077;
(Continued)

(56) References Cited

U.S. PATENT DOCUMENTS 5,437,664 A * 8/1995 Cohen ................ A61B 18/1492
606/49
8,162,932 B2 * 4/2012 Podhajsky ......... A61B 18/1206
606/34
(Continued)

OTHER PUBLICATIONS

International Search Report and Written Opinion, dated May 31, 2022, received in connection with corresponding International Patent Application No. PCT/US2021/065613.

*Primary Examiner* — Joseph A Stoklosa
*Assistant Examiner* — Annie L Shoulders
(74) *Attorney, Agent, or Firm* — Meunier Carlin & Curfman LLC (57) ABSTRACT

The present invention is directed to a system and method for adaptive multivariate control for performing a radiofrequency (RF) ablation procedure with an energy delivery device. The system includes an energy source for delivering energy to a patient's body; one or more energy delivery devices; two or more sensors for measuring at least two factors related to an ablation procedure, respectively; and at least one processor. The method includes steps of: measuring at least two factors related to an ablation procedure; determining a first operating threshold based, at least in part, on a first factor; controlling an energy delivery device based on the first operating threshold to create a lesion at the target site within the patient; determining a second operating threshold based, at least in part, on a second factor; switching control of the energy delivery device from the first factor to the second factor; and controlling the energy delivery device based on the second operating threshold to create a lesion at the target site within the patient. The present invention is also directed to a RF probe configured to be used with the adaptive multivariate control system and method to perform RF ablation procedures.

14 Claims, 6 Drawing Sheets

(52) U.S. Cl.
CPC ............... *A61B 2018/00065* (2013.01); *A61B 2018/00077* (2013.01); *A61B 2018/00095* (2013.01); *A61B 2018/00577* (2013.01); *A61B 2018/00666* (2013.01); *A61B 2018/00779* (2013.01); *A61B 2018/00821* (2013.01); *A61B 2018/00827* (2013.01); *A61B 2018/00875* (2013.01); *A61B 2018/00886* (2013.01); *A61B 2018/00892* (2013.01); *A61B 2218/002* (2013.01); *A61B 2218/007* (2013.01)

(58) Field of Classification Search
CPC  A61B 2018/00095; A61B 2018/00577; A61B 2018/00666; A61B 2018/00779; A61B 2018/00821; A61B 2018/00827; A61B 2018/00875; A61B 2018/00886; A61B 2018/00892; A61B 2218/002; A61B 2218/007
See application file for complete search history.

(56) References Cited

U.S. PATENT DOCUMENTS

| | | | |
|---|---|---|---|
| 2012/0022520 A1* | 1/2012 | Bek | A61B 18/1485 606/41 |
| 2015/0157388 A1 | 6/2015 | Mehta et al. | |
| 2015/0289930 A1* | 10/2015 | Elgaard | A61B 18/1492 606/40 |
| 2018/0092689 A1* | 4/2018 | Tegg | A61B 18/1492 |
| 2018/0338793 A1* | 11/2018 | Sulkin | A61B 18/1492 |
| 2019/0223944 A1* | 7/2019 | Coates | A61N 7/022 |
| 2023/0083584 A1* | 3/2023 | Del Cid | A61B 18/1206 |

\* cited by examiner

FIG. 8

RADIOFREQUENCY PROBE, SYSTEM, AND METHOD FOR ADAPTIVE MULTIVARIATE CONTROL OF AN ABLATION PROCEDURE

FIELD OF THE INVENTION

The subject matter of the present invention relates generally to adaptive multivariate control of an ablation procedure and a radiofrequency probe, system, and method therefor.

BACKGROUND

Radiofrequency (RF) ablation is a treatment modality designed to thermally destroy unwanted biological tissue, and is used to treat a variety of diseases, including tumors, cardiac arrhythmias, and pain. The modality treats pain by lesioning a section of a nerve that is interposed between the pain source and the brain. That is, the lesion prevents the transmission of pain signals originating in the periphery of the nervous system from reaching higher-order neurological structures that are required for perception.

In an RF ablation procedure, an RF ablation system generates and delivers radiofrequency energy to the targeted biological tissue. The RF ablation system includes an external radiofrequency generator, at least one needle-like electrode, often called a probe, and a secondary electrode. The secondary electrode may take the form of a large dispersive electrode, also known as a ground pad, which is placed on the surface of the patient's body, or a second needle-like electrode or probe. The probe generally has an insulated shaft with an exposed conductive tip to deliver RF energy.

The ablation procedure includes placing the first needle-like electrode or probe at or near a target ablation site and placing the secondary electrode somewhere on or in the patient's body. The generator will deposit an electrical charge on the electrode pair, and the polarity of the charge is then alternated in the RF range, i.e. between 100 kHz and 1 GHz and more specifically between 300-600 kHz. The alternating charge causes ions (Na+, K+, Cl−) within the tissue to move, analogous to an electrical current. Resistance to the electrical current causes frictional heating, the coagulation of cells and the formation of a lesion that effectively denervates the neural structure in question. Tissue temperatures below about 45° C. are considered to be non-destructive, while temperatures above 100-110° C. cause tissue vaporization, and with very high energy densities, tissue carbonization (i.e., tissue charring). Tissue carbonization is an irreversible process that limits further energy deposition and can stunt lesion development (i.e. shape, volume).

RF ablation control systems typically use one of three methods to control the energy that is delivered to biological tissue: power-control, temperature-control, or impedance-control. The power-controlled system varies the electrical voltage applied to the tissue to maintain a constant RF power. The temperature-controlled system varies the RF energy that is delivered to tissue to maintain a "fixed" set temperature. In this case, a sensor (e.g., a thermocouple) is integrated into the probe to measure tissue temperature. The impedance-controlled system adjusts the amount of RF energy that is delivered to the tissue depending on the tissue's impedance (measured between the stimulating electrodes). The tissue's impedance is sensitive to changes in the ablative environment (migration of surrounding conductive ions, desiccation, vaporization, carbonization), and can be used to describe lesion progress. An increasing tissue impedance generally indicates lesion formation, but too high of an impedance occurring early in the treatment makes it difficult to transfer the RF energy past the interface between the tissue and the electrode, limiting lesion development. In an impedance-controlled system, when the tissue impedance rises and exceeds a certain threshold, then the RF energy delivery is shut-down, allowing the vapor to settle, and then is re-applied at a lower power level.

The various RF control systems and probe designs that are used today, as described above, operate in a power-forward manner and cannot optimize lesion formation since they do not accommodate for lesion site variability (i.e., differences in tissue between nerve; bone; blood; fat, etc.) and/or the changes that occur during treatment (e.g., liquid formation around the probe tip and/or thermocouple; vaporization; carbonization, etc.). For instance, the power- and thermally controlled systems deliver a constant power and set temperature (respectively) to tissue based on characterized standards, and do not adjust stimulation energy in real-time based on feedback from direct measures of lesion formation (i.e., impedance; vapor, etc). Incidentally, impedance spikes are rarely observed during the formation of lesions with power- and temperature-controlled systems, suggesting that power-controlled and temperature-controlled systems do not deliver enough energy to fully lesion treated tissue. Moreover, impedance-controlled systems do not consider the amount of time that tissue is at temperatures necessary to irreversibly destroy nervous tissue. Instead, impedance-controlled systems rely on impedance measurements that are variable and susceptible to artifact.

Thus, the art is continuously seeking new and improved systems and methods for treating pain using RF ablation, and more particularly to RF control systems, probes and methods that are optimized to evaluate, accommodate for and adapt to the changing tissue environment during the ablation procedure.

SUMMARY

Objects and advantages of the invention will be set forth in part in the following description, or may be obvious from the description, or may be learned through practice of the invention.

The present invention is directed to a radiofrequency (RF) ablation system for performing an RF ablation procedure. The RF ablation system includes: an energy source for delivering energy to a target site of a patient's body and one or more energy delivery devices electrically coupled to the energy source. The RF ablation system further includes two or more sensors for measuring at least two factors, respectively, related to the RF ablation procedure. The RF ablation system additionally includes at least one processor configured to perform a plurality of operations. The plurality of operations include: (i) measuring the at least two factors related to the RF ablation procedure; (ii) determining a first operating threshold for the energy delivery device based, at least in part, on a first factor of the at least two factors; (iii) controlling the energy delivery device based on the first operating threshold to create a lesion at the target site within the patient; (iv) determining a second operating threshold for the energy delivery device based, at least in part, on an additional factor of the at least two factors; (v) switching control of the energy delivery device from the first factor to the additional factor; and (vi) controlling the energy delivery device based on the second operating threshold to further develop the lesion at the target site within the patient.

In one particular embodiment, the at least two factors can include at least two of: power, current, voltage, impedance, temperature of tissue at the target site, temperature of a coolant associated with a cooling device for the RF ablation procedure, duration (time) of stimulation, rate of current change, rate of voltage change, rate of power change, rate of temperature change of the tissue at the target site, rate of temperature change of the coolant, pressure at the target site, gas formation at the target site, rate of change of gas formation at the target site, or a combination thereof. Further, one of the at least two factors can be rate of change of tissue impedance.

In another embodiment, the system can be configured to continuously monitor and record the at least two factors.

In an additional embodiment, the first factor can be a tissue temperature at the target site.

In a further embodiment, the additional factor can be tissue impedance or rate of change of tissue impedance at the target site within the patient.

In yet another embodiment, the system can be configured to determine at least one additional operating threshold for the energy delivery device based, at least in part, on a third factor; and switch control of the energy delivery device from the first operating threshold or the second operating threshold to the third operating threshold to further develop the lesion at the target site.

In still another embodiment, at least one sensor of the two or more sensors can be configured to measure a respective factor related to the ablation procedure at the target site.

In an additional embodiment, the one or more energy delivery devices can include an RF probe comprising: an elongate member having a proximal end and a distal end, the distal end comprising an electrically and thermally-conductive energy delivery device for delivering one of electrical and RF energy to a patient's body, the RF probe having at least one electrode and an electrically and thermally-conductive portion having a temperature sensing element; and one or more ablation enhancing features comprising: a cooling device extending within the elongate member, a suction mechanism having a suction path, a fluid injection mechanism having a fluid path, and/or a directional energy delivery mechanism. Further, the two or more sensors can include, at least, a thermocouple positioned on the RF probe.

In one more embodiment, the system can be configured to switch control of the energy delivery device from the first factor to the additional factor after the first operating threshold is reached.

The present invention is further directed to a radiofrequency (RF) probe. The RF probe includes: an elongate member having a proximal end and a distal end, the distal end comprising an electrically and thermally-conductive energy delivery device for delivering one of electrical and radiofrequency energy to a target site of a patient's body, the electrically and thermally-conductive energy delivery device having an electrically and thermally-conductive portion having at least one electrode and a temperature sensing element; and at least one ablation enhancing feature configured to improve the formation of a lesion when the RF probe is applied to a patient's tissue in an ablation procedure.

In one particular embodiment of the RF probe, the at least one electrode can be porous. Further, the at least one ablation enhancing feature can include a suction mechanism having a suction path, wherein the suction path is defined by the interior of the elongate member extending from the distal end to the proximal end. Moreover, the at least one ablation enhancing feature can include a fluid injection mechanism having a fluid path, wherein the fluid path is defined by the interior of the elongate member extending from the distal end to the proximal end.

In another embodiment, the at least one ablation enhancing feature can include a suction mechanism having a suction path and/or a fluid injection mechanism having a fluid path. Further, the RF probe can further include an additional electrode disposed within the suction path and/or the fluid path. Moreover, the suction path can include a suction channel within the elongate member and the fluid path comprises a fluid channel within the elongate member.

In an additional embodiment, the at least one ablation enhancing feature can be defined by the electrode being formed in a geometric shape extending along a portion of the elongate member such that the electrode is configured to individually target rotational sections of the patient's tissue surrounding the elongate member.

In yet another embodiment, the at least one ablation enhancing feature can include a plurality of secondary electrodes composed of tines extending from the elongate member which are configured to surround a target patient tissue area in a three-dimensional orientation.

In one more embodiment, the elongate member can further include one or more internal lumens for containing a coolant therein.

The present invention is further directed to a method for performing a radiofrequency (RF) ablation procedure with a RF probe. The method includes steps of:

measuring at least two factors related to an ablation procedure;

determining a first operating threshold for the RF probe based, at least in part, on a first factor;

controlling the RF probe based on the first operating threshold to create a lesion at a target site within the patient;

determining a second operating threshold for the RF probe based, at least in part, on a second factor;

switching control of the RF probe from the first factor to the second factor; and controlling the RF probe based on the second operating threshold to further develop the lesion at the target site within the patient.

In one particular embodiment, the step of switching control of the RF probe from the first factor to the second factor can occur after the first operating threshold is reached.

In another embodiment, the method can further include steps of:

collecting data relating to operation of the RF probe during the measuring, determining first and second operating thresholds, controlling, and switching steps;

inputting the collected data into a deep learning network configured to learn the measuring, determining first and second operating thresholds, controlling, and switching steps relating to the RF ablation procedure; and controlling the RF probe based on the deep learning network.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this invention, a lesion refers to the region of tissue that has been irreversibly damaged as a result of the application of thermal energy, and the invention is not intended to be limited in this regard. Furthermore, for the purposes of this description, proximal generally indicates that portion of a device or system next to or nearer to a handle of the probe (when the device is in use), while the term distal generally indicates a portion further away from the handle of the probe (when the device is in use).

As used herein, the terms "about," "approximately," or "generally," when used to modify a value, indicates that the value can be raised or lowered by 5% and remain within the disclosed embodiment. Further, when a plurality of ranges are provided, any combination of a minimum value and a maximum value described in the plurality of ranges are contemplated by the present invention. For example, if ranges of "from about 20% to about 80%" and "from about 30% to about 70%" are described, a range of "from about 20% to about 70%" or a range of "from about 30% to about 80%" are also contemplated by the present invention.

Generally speaking, the present invention is directed to a system and method for adaptive multivariate control for performing a radiofrequency (RF) ablation procedure with an RF probe. The system includes an energy source for delivering energy to a patient's body; one or more energy delivery devices electrically coupled to the energy source; two or more sensors for measuring at least two factors related to an ablation procedure, respectively, and at least one processor configured to perform a plurality of operations for controlling a RF ablation procedure. The method includes steps of: measuring at least two factors related to an ablation procedure; determining a first operating threshold for the RF probe based, at least in part, on a first factor; controlling the RF probe based on the first operating threshold to create a lesion at the target ablation site within the patient; determining a second operating threshold for the RF probe based, at least in part, on a second factor; switching control of the RF probe from the first factor to the second factor; and controlling the RF probe based on the second operating threshold to create a lesion at the ablation site within the patient. The present invention is also directed to a RF probe and a RF ablation system configured for adaptive multivariate control. The present inventors have found that the adaptive multivariate control of RF ablation, such as using the control system, probe and method of the present invention, enables optimization of lesion formation during the ablation of biological tissue. In particular, the adaptive multivariate control of RF ablation enables the ablation procedure to 'listen' to the tissue at the target site, especially the changing tissue conditions at the target site, to determine how to direct and control delivery of RF energy to the target site. The specific features of the RF ablation probe, system and method of the present invention may be better understood with reference to FIGS. 1-8.

Figure 1:
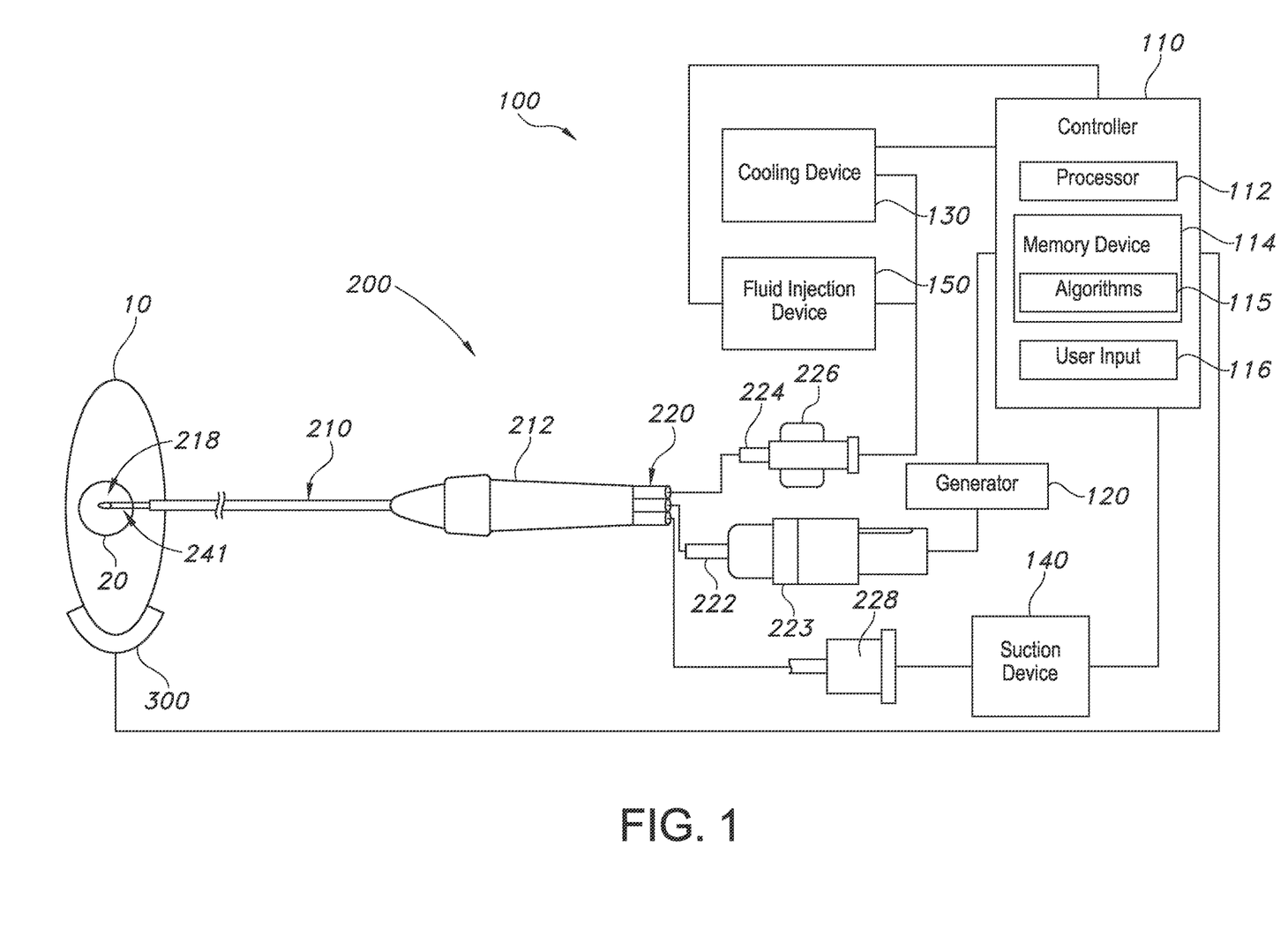
FIG. 1 illustrates a diagram of a radiofrequency (RF) ablation system according to one particular embodiment of the present invention.

Referring now to the drawings, FIG. 1 illustrates a schematic diagram of one embodiment of a system 100 of the present invention. As shown, the system 100 includes a controller 110, a generator 120, and at least one energy delivery probe 200. The system additionally includes at least one secondary electrode, e.g., grounding pad 300 as shown in FIG. 1, or a second probe 200 (not shown). The system 100 may optionally include one or more of a cooling device 130, a suction device 140, and a fluid injection device 150. Additionally, in aspects of the invention, more than one probe 200 may be present in the system 100. As shown in the illustrated embodiment, the generator 120 is a radiofrequency (RF) generator, but may optionally be any power source for a delivery device that may deliver other forms of energy, including but not limited to microwave energy, thermal energy, ultrasound and optical energy. Further, the controller 110 and/or the generator 120 may include a display incorporated therein. The display may be operable to display various aspects of a treatment procedure, including but not limited to any parameters that are relevant to a treatment procedure, such as temperature, impedance, etc. and errors or warnings related to a treatment procedure. If no display is incorporated into the controller 110 and/or the generator 120, the controller 110 and/or the generator 120 may include means of transmitting a signal to an external display. In one embodiment, the controller 110 is operable to communicate with one more devices, for example with one or more energy delivery probes 200 and the generator 120, the cooling device 130, the suction device 140 and/or the fluid injection device 150. Such communication may be unidirectional or bidirectional depending on the devices used and the procedure performed. The controller 110 may include a processor 112, a memory device 114 storing one or more control algorithms 115, and a user input 116, such as a control button, touch screen, or other user input.

The energy delivery probe(s) 200 may include any means of delivering energy to a target region of tissue 20 of a patient's body 10 adjacent to the distal tip region 218. For example, the probe(s) 200 may include an ultrasonic device, an electrode or any other energy delivery means and the invention is not limited in this regard. Similarly, energy delivered via the probe(s) 200 may take several forms including but not limited to thermal energy, ultrasonic energy, radiofrequency energy, microwave energy or any other form of energy. For example, in one embodiment, the active region 218 of the probe(s) 200 may include an electrode 241. As described in further detail below with regard to FIGS. 2-3, the active region 218 of the electrode may be 2 to 20 millimeters (mm) in length and energy delivered by the electrode is electrical energy in the form of current in the RF range. The size of the active region 218 of the electrode can be optimized for placement in a specific anatomical target location 20, such as within an intervertebral disc; however, different sizes of active regions, all of which are within the scope of the present invention, may be used depending on the specific procedure being performed. In some embodiments, feedback from the generator 120 may automatically adjust the exposed area, i.e., active region or tip 218, of the probe(s) 200 in response to a given measurement such as impedance or temperature. For example, in one embodiment, the probe 200 may maximize energy delivered to the tissue by implementing at least one additional feedback control, such as a rising impedance value.

Figure 2:
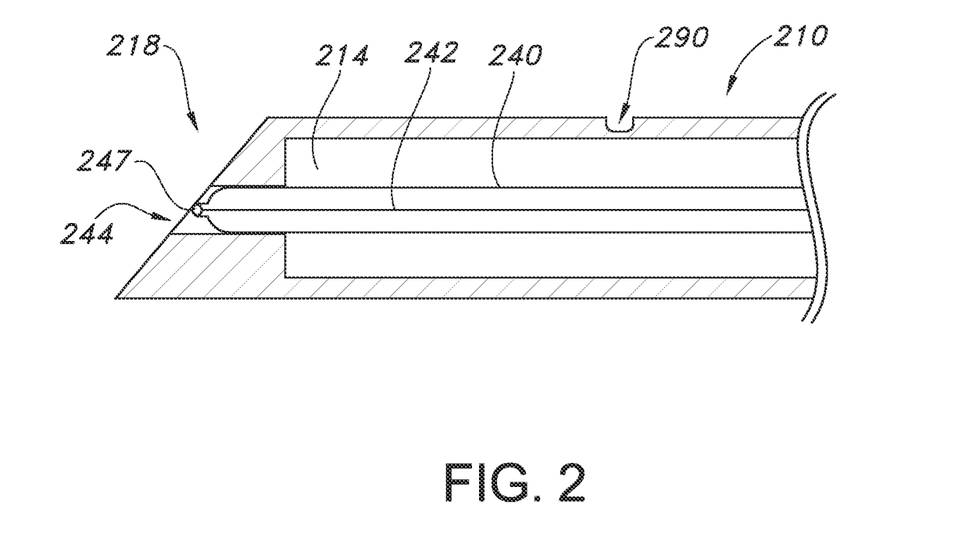
FIG. 2 illustrates a side cut-away view of the active tip of one embodiment of a RF probe configured for use with the system of FIG. 1.

Referring now to FIGS. 1-2, one embodiment of a radiofrequency energy delivery probe 200 of the present invention is shown in greater detail. As shown, the probe 200 includes a handle 212, an elongated member 210, and a cable-tubing assembly 220. The cable-tubing assembly 220 can communicate with the handle 212 at one end of the handle 212. The elongated member 210 can communicate with the handle 212 at an opposite end of the handle 212. As shown in FIG. 1, the cable-tubing assembly 220 includes an electrical cable 222 and, optionally, fluid tubing 224 in communication with a fluid injection device 150 and/or a cooling device 130 that recirculates cooling fluid. The electrical cable 222 can include an insulating jacket constructed from, for example, polyvinyl chloride (PVC) or any other suitable material. The electrical cable 222 can terminate at a proximal end at an electrical connector 223. The electrical connector 223 can be, for example, a circular electrical connector as shown in FIG. 2 configured to be placed in electrical communication with an electrical connection of the generator 120. The fluid tubing 224 can be constructed from one or more lumens, such as dual-lumens having walls constructed from clear polyvinyl chloride (PVC). The walls of the dual-lumen tubing can optionally be thermally bonded together. The dual-lumen fluid tubing 224 can terminate at a proximal end at a connector 226, such as a female or male Luer connector. Additionally, a cap, e.g. a vented cap (not shown), can be provided to cover or seal the connector 226. The cap can be made from nylon or other suitable material and can have a different color or opacity than the connector 226.

The cable-tubing assembly 220 can be flexible due to the flexible materials of the insulating jacket of the electrical cable 222 and the walls of the lumen 224. The cable-tubing assembly 220 can optionally be bonded between the insulating jacket of the electrical cable 222 and the wall of at least one lumen of the fluid tubing 224 along the length of the assembly 220. The bonding can be done, for example, by heat welding, UV adhesive, or any other suitable form of welding or bonding plastic or polymeric materials together.

FIG. 2 further illustrates the active tip 218 of the elongate member 210 of the probe 200. The elongate member 210 has an active tip 218 configured for delivery of RF energy located at a distal end thereof. In particular, an electrode 241 may be formed at the active tip 218. A lumen 214 is formed within the elongate member 210 extending along the length of the elongate member 210. The elongated member 210 includes a thermocouple hypotube 240 extending the length of the elongate member 210 and having a wire 242, such as a constantan wire, extending therethrough. The constantan wire 242 may form a thermocouple 247 at the distal end of the active tip 218 of the elongate member 210, and extend through the elongate member 210 to the electrical cable 222 to sense the temperature at the active tip 218 and transmit temperature information to the controller 110. The wire 242 can be welded to the thermocouple hypotube 240 at the distal end 218 of the elongate member 210 to form a thermocouple 247. The thermocouple 247 may function as a temperature sensing element to sense the temperature of the patient's tissue and the temperature of the active distal tip 218 of the elongate member 210. Optionally, as shown in FIG. 2, the elongate member 210 may include a distal opening 244 and/or one or more apertures 290 in fluid communication with the lumen 214. The distal opening 244 and/or apertures 290 enable suction and/or the delivery of fluid to or from the target area 20, e.g., when the probe 200 is in communication with a fluid injection device 150 and/or a suction device 140.

Figure 3:
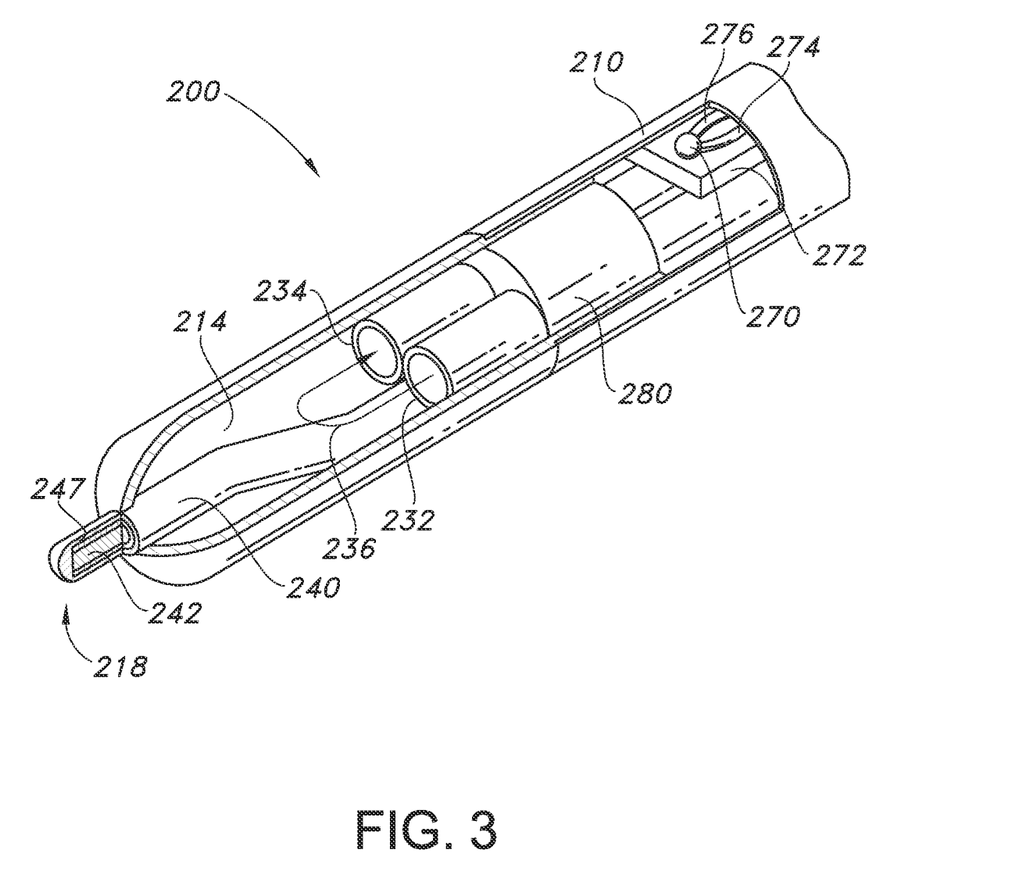
FIG. 3 illustrates a perspective cut-away view of the active tip of another embodiment of a RF probe configured for use with the system of FIG. 1 having cooling fluid inlet and outlet channels.

FIG. 3 illustrates a perspective cut-away view of the active tip 218 of the elongated member 210 of the probe 200 in another embodiment of the invention where the probe 200 is a cooled probe that is cooled by circulation of fluid within the elongate member 210. As with the probe 200 illustrated in FIG. 2, the elongated member 210 includes a thermocouple hypotube 240 extending the length of the elongate member 210 and having a wire 242 extending therethrough. The tube 240 may be made from, for example, stainless steel or other suitable material. The wire 242 may be a constantan wire. The wire 242 may be a solid wire or a porous wire, as will be described in further detail below. When the wire 242 is porous, forming a porous electrode 241, the electrode 241 may include a distal opening 244. The wire 242 can be welded to the thermocouple hypotube 240 at the distal end 218 of the elongate member 210 to form a thermocouple 247. The thermocouple 247 may protrude beyond the distal end 218 of the elongate member 210. In addition, the length of the thermocouple 247 may be chosen to assist in creating lesions of different sizes. For example, in such embodiments, a user may select one or more probes from a plurality of probes having different lengths based on, e.g. a desired lesion size and/or a desired rate of power delivery based on a treatment procedure type of the tissue. In particular embodiments, the length of the thermocouple 247 be less than about 1 mm, for instance the length of the thermocouple 247 may range from about 0.20 mm to about 0.70 mm. In some aspects of the invention, the thermocouple 247 may also have a different shape or volume. Thus, since an actual lesion size will vary with the lengths of the thermocouple 247, a thermocouple 247 having a longer length can be configured to generate lesions of smaller sizes, whereas a thermocouple 247 having a shorter length can be configured to generate lesions of larger sizes.

Accordingly, varying the length of the thermocouple 247 can control and optimize the size of the lesion for different anatomical locations, for instance creating smaller lesions in regions adjacent to critical structures such as arteries and motor nerves. Thus, the range of lengths of the thermocouple 247 of the present disclosure provide several advantages including for example, the ability to create custom lesion volumes for different procedures (i.e. the control of the lesion volume is intrinsic to the mechanical design of the probe, which is independent of the generator and algorithms). Moreover, the different lengths of the thermocouple 236 creates a mechanical safety mechanism to prevent over-ablation in sensitive anatomical regions.

In addition, the length of the thermocouple 247 is configured to increase (or decrease) a power demand of the elongate member 210. Further, as shown, whereby the thermocouple 247 includes a stainless steel hypotube 240, the hypotube 240 may be electrically conductive and may be electrically coupled to the elongate member 210 to form the electrode 241. Placing the thermocouple 236 at the distal active tip 218, rather than within a lumen or volume 214 defined by the elongate member 210, may be beneficial because it allows the thermocouple 247 to provide a more accurate indication of the temperature of tissue proximate to the distal tip 218. This is because, when extended beyond the distal tip 218, the thermocouple 247 will not be as affected by the cooling fluid flowing within the volume 214 as it would be were it located within volume 214. Thus, in such embodiments, the probe 200 may include a protrusion formed by the distal tip 218 protruding from the distal region of the elongate member 210, whereby the protrusion is a component of the thermocouple 247.

In one embodiment, the thermocouple 247 is connected to the generator 120 and/or controller 110 via the cable 222 of the cable-tubing assembly 220 although any means of communication between the thermocouple 247 and the generator 120 and/or controller 110, including wireless protocols, are included within the scope of the present invention.

FIG. 3 further illustrates a fluid inlet tube 232 and a fluid return tube 234 extending within the elongate member 210 to the distal active tip 218. The fluid inlet tube 232 is configured to circulate cooling fluid from the cooling device 130 into the distal active tip 218, where the fluid can flow within the interior lumen 214 of the elongate member 210 and be returned through the return tube 234 to the cooling device 130. The fluid inlet tube 232 and the fluid return tube 234 are bonded to the fluid tubing 224 using connecting means (not shown) to form a fluid-tight seal. The connecting means can be any means of connecting two tubes including but not limited to ultraviolet (UV) glue, epoxy or any other adhesive as well as friction or compression fitting. For example, the tubes 232 and 234 may be bonded to the fluid tubing 224 by medical grade adhesives (not shown).

Referring still to FIG. 3, the probe 200 may further include one or more secondary temperature sensing elements 270 located within the elongate member 210 at some distance away from the distal tip 218, and positioned adjacent a wall of the elongate member 210. The secondary temperature sensing elements 270 may similarly include one or more thermocouples, thermometers, thermistors, optical fluorescent sensors or any other means of sensing temperature. For example, as shown, the secondary temperature sensing element 270 is a thermocouple made by joining copper and constantan thermocouple wires, designated as 274 and 276 respectively. Further, in certain embodiments, the copper and constantan wires 274 and 276 may extend through a lumen of the elongate member 210 and may connect to the electrical cable 222 of the cable-tubing assembly 220.

In addition, the probe 200 may further include a thermal insulator 272 located proximate to any of the temperature sensing elements 270. As such, the thermal insulator 272 may be made from any thermally insulating material, for example silicone, and may be used to insulate any temperature sensing element from other components of the probe 200, so that the temperature sensing element will be able to more accurately measure the temperature of the surrounding tissue. More specifically, as shown, the thermal insulator 272 is used to insulate the temperature sensing element 270 from cooling fluid passing through the fluid inlet tube 232 and the fluid return tube 234.

In some embodiments of the invention, the one or more secondary temperature sensing elements 270 may be the only temperature sensing elements, and the thermocouple 247 at the distal end 218 may be omitted from the probe 200. For instance, in embodiments in which the probe 200 is intended to be able to contact with bone (i.e., osseous tissue or periosteum), one or more temperature sensing elements 270 along the probe 210 can be beneficial. In contrast, a thermocouple 247 at the distal end 218 of the probe 200 cannot touch bone, so a user cannot positively affirm via direct contact that the position of the probe 200 is stable and ready to deliver without falling out of position. However, positioning the one or more temperature sensing elements 270 along the length of the elongate member 210 can eliminate such potential problems.

In further embodiments, the elongate member 210 of the probe 200 may also include a radiopaque marker 280 incorporated somewhere along the elongate member 210. For example, as shown, in FIG. 3, an optimal location for a radiopaque marker may be at or proximate to the distal tip region 218. The radiopaque markers are visible on fluoroscopic x-ray images and can be used as visual aids when attempting to place devices accurately within a patient's body. These markers can be made of many different materials, as long as they possess sufficient radiopacity. Suitable materials include, but are not limited to silver, gold, platinum and other high-density metals as well as radiopaque polymeric compounds. Various methods for incorporating radiopaque markers into or onto medical devices may be used, and the present invention is not limited in this regard.

Figure 4A:
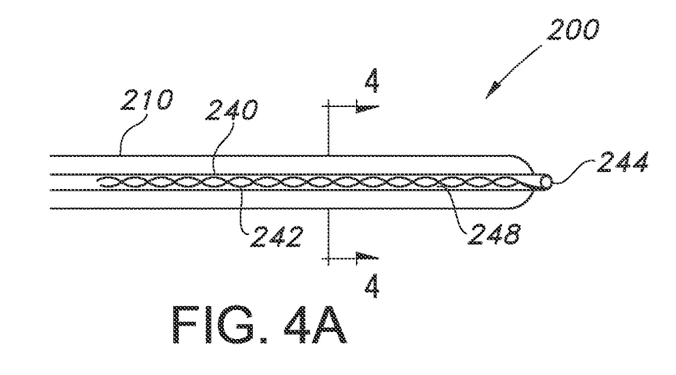
FIG. 4A illustrates a side cut-away view of an embodiment of an active tip of the RF probe of FIG. 2.
Figure 4B:
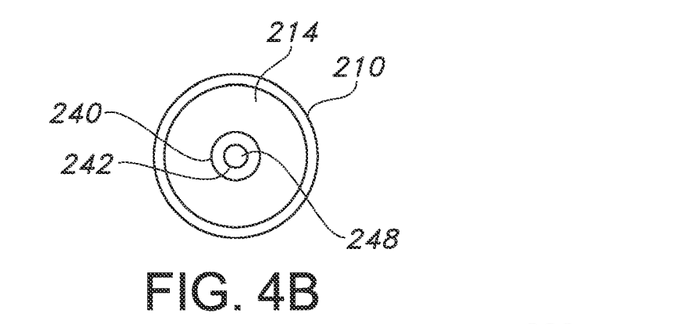
FIG. 4B illustrates a cross-sectional view of the active tip of FIG. 4A taken along line 4-4.

FIGS. 4A-B and 5A-B illustrate embodiments of the elongate member 210 having a porous electrode 241 and a solid-wire electrode 241, respectively. FIG. 4A shows a side cut-away view of the elongate member 210 having a porous electrode 241 within a hollow space 248 of the hypotube 240. The porous electrode may be formed from a wire mesh and/or braided wire or may be an open coil electrode formed as a helix that is loosely wound. FIG. 4B shows a cross-sectional view of the elongate member of FIG. 4A taken along the line 4-4, illustrating the hypotube 240 within the inner lumen 214 of the elongate member 210. The porous electrode can be disposed within the hollow space 248 of the hypotube 240. As shown in FIG. 4A, there may be an opening 244 into the hypotube 240 at the distal end. Such arrangement shown in FIG. 4A-B may enable a suction device 140 and/or a fluid injection device 150 to suction and/or inject fluid directly through the tube 240 by delivering and/or removing fluid through the hollow space 248. The suction device 140 and fluid injection device 150 are each ablation enhancing features that are configured to assist in the further development of a lesion in patient tissue during an ablation procedure.

Figure 5A:
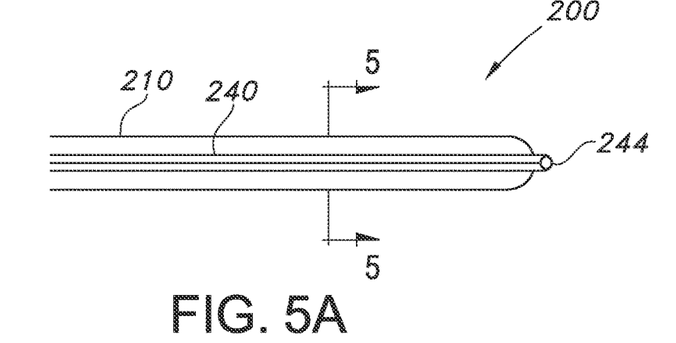
FIG. 5A illustrates a side cut-away view of an embodiment of an active tip of the RF probe of FIG. 2.
Figure 5B:
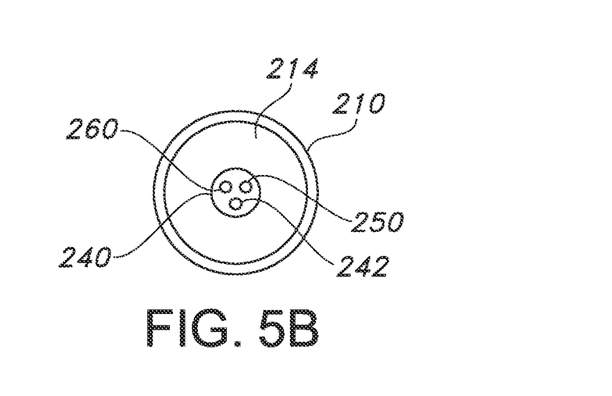
FIG. 5B illustrates a cross-sectional view of the active tip of FIG. 5A taken along line 5-5.

FIGS. 5A-B illustrate embodiments of the elongate member 210 having a solid-wire electrode 242. FIG. 5A shows a side cut-away view of the elongate member 210 having a solid wire electrode 242 within the hypotube 240. The hypotube 240 may additionally include a suction channel 250 and/or a fluid injection channel 260 configured for suctioning and/or delivering fluid to the patient's tissue via an opening 244 at the end of the hypotube 240. In this aspect, both suction and fluid injection could be performed within the same procedure, e.g., simultaneously or in an alternating arrangement.

For instance, a suction device 140 can be provided that may be in communication with the suction channel 250 of the probe 200, e.g., via a suction connector 228, and the controller 110 of the system 100. By providing a suction device 140 including a suction path within the elongate member 210, as described above, fluids (liquids and gases) can be shunted away from the conductive surface of the ablation electrode 241. By directing liquids and gases away from the conductive surface of the ablation electrode 241, the variability of energy delivered from the electrode 242 to the tissue can be reduced. The suction device 140 may further include one or more sensors (not shown) for monitoring the pressure of the suction and/or the pressure within the lumen 214 of the elongate member 210 and in the target area 20 of tissue.

The suction device 140 of the present invention may further include one or more electrodes (not shown) disposed within the suction path, e.g., within the hypotube 240 or within a suction channel 250, if present. The electrode(s) within the suction path may assist the system 100 with monitoring vapor presence at the lesion site and assessing the extent of lesion formation. By assessing the extent of lesion formation, the electrode(s) within the suction path can function as an ablation enhancing feature. In particular, the system 100 may compare the impedance values measured using the electrode 242 with impedance values measured by an electrode within the suction path in order to determine lesion completeness. If the ablation electrode 242 has a lower impedance value than the impedance measured by an electrode within the suction path, then the lesion is incomplete. If the impedance values of both the ablation electrode 242 and an electrode within the suction path are high, then the lesion is complete. Because the completeness of the lesion can be monitored, the total duration of ablation time may be reduced if the lesion is determined to be complete.

Figure 6:
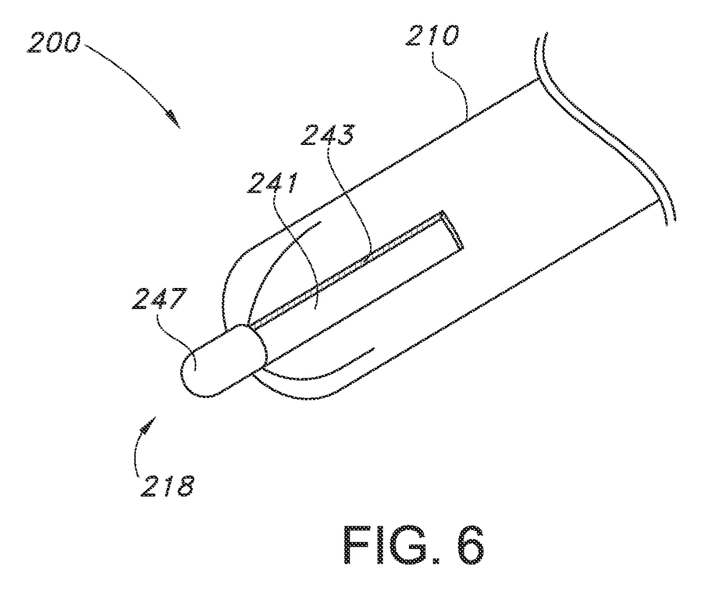
FIG. 6 illustrates a perspective view of another embodiment of an active tip of the RF probe having a directional energy delivery mechanism.

In another aspect of the present invention, as shown in FIG. 6, the probe(s) 200 can include a directional energy delivery mechanism formed by a directional electrode 241. For instance, the electrode 241 can be formed in a geometric shape extending along a portion of the elongate member 210 such as a longitudinal stripe along the elongate member 210. As shown in FIG. 6, the electrode 241 can extend along a portion of the elongate member 210 at the active tip 218, where the electrode 241 is exposed beneath an insulating layer 243 surrounding the elongate member 210. In this configuration, the electrode 241 can be configured to individually target rotational sections of the patient's tissue surrounding the elongate member 210 as the elongate member 210 is rotated within the target area 20 during an ablation procedure. Since energy is not delivered to the target area 20 all at once, vaporization of tissue is localized, and the vapor may shunt to immediately adjacent tissue that has yet to be lesioned. Using the electrode 241, tissue impedance can be measured at each rotational position to ensure that a maximal lesion has been formed all around the elongate member 210 of the probe 200. As a result, manipulation of the directional electrode 241 can be used to ensure a uniform lesion 360 degrees around the electrode despite any local differences in tissue properties. As the energy of the directional electrode 241 can focus on one rotational region of the lesion at a time, differing amounts of energy can be delivered to each rotational region in order to ultimately ensure similar tissue impedance measures and lesion consistency in each rotational region.

Figure 7:
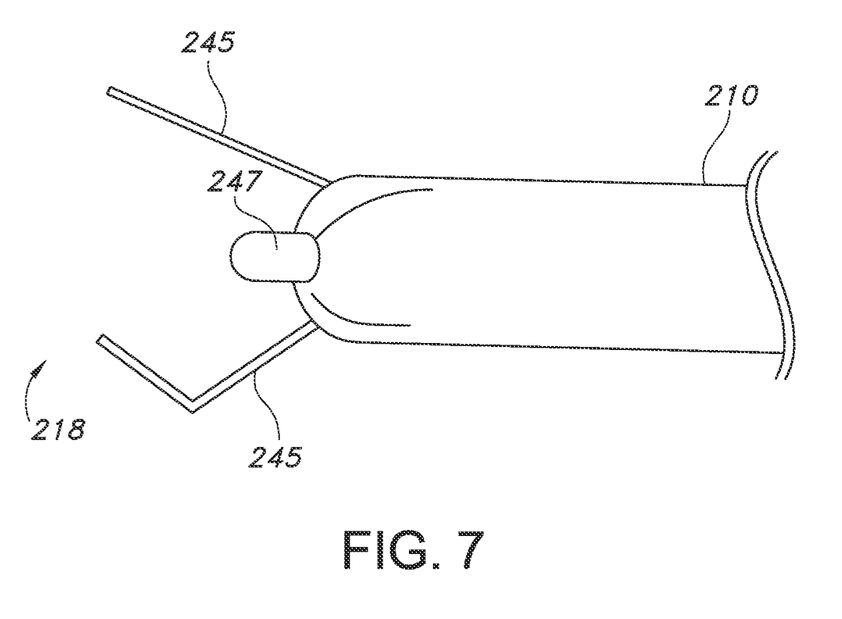
FIG. 7 illustrates a perspective view of another embodiment of an active tip of the RF probe having one or more secondary electrodes extending from the elongate member.

In a further aspect of the invention, as shown in FIG. 7, the elongate member 210 of a probe 200 may include a first electrode 241 at the distal active tip 218 of the elongate member 210 and one or more secondary electrodes 245 extending from the elongate member 210. For instance, the one or more secondary electrodes 245 can extend from the distal end 218 of the elongate member 210. As shown in FIG. 7, the secondary electrodes 245 can be in the form of two or more tines 245 configured to surround the target area 20 in a three-dimensional orientation. The tines 245 can be straight or have an angled or curved configuration, as shown in FIG. 7. In such an arrangement, RF energy can be pulsed back and forth between each of the tines 245 and/or pulsed between one or more of the tines 245 and the first electrode 241. Each of the electrodes 241 and 245 may be configured to deliver RF energy and measure the biological factors at the target area 20, e.g., tissue temperature and tissue impedance, in an independent fashion.

As described above, the system 100 may include a cooling device 130 configured to reduce a temperature of material located at and proximate to one or more of the probes 200. For example, the cooling device 130 may include circulating a cooling fluid through the elongate member 210, such as by circulating a fluid through the inlet 232 and outlet 234 tubes via one or more pumps (not shown). Additionally or alternatively, the cooling device 130 may include a heat transfer material and/or a heat sink disposed within the elongate member 210. For instance, a heat sink may include a phase change material. In one particular embodiment, about 1 gram to about 12 grams of the phase change material may be required to remove from about 2 Watts to about 12 Watts of energy from the probe 200 over a 150 second time period. One exemplary phase change material may comprise paraffin wax. In alternative arrangements, a heat sink may include a heat sink external to the probe 200 and/or an endothermic reaction system. The cooling device 130 may additionally or alternatively include a heat transfer material such as a thermally conductive material, e.g., a metal, a ceramic material, or a conductive polymer, or one or more Peltier circuits.

As described above, the system 100 may additionally include a fluid injection device 150, e.g., by delivering fluid through the elongate member such as via a fluid injection channel 260. In contrast to the cooling device 130, which circulates fluid within the probe(s) 200 to cool the probe(s) and the tissue at the lesion site, the fluid injection device 150 may deliver fluid through the probe 200 to the patient's tissue at the lesion site, e.g., through the opening 244 at the tip of the electrode 241. The fluid injected into the lesion site may cool the lesion site near the electrode 241, thereby allowing higher currents to pass into more distal tissue and grow the lesion before any vaporization or desiccation near the electrode 241 occurs. Additionally, if a high conductivity fluid is introduced via the fluid injection device 150, the high conductivity fluid may contribute to the formation of the lesion and deactivate nearby nerve cells by way of ionic and osmotic imbalance. The delivered fluid may displace vapor pockets and penetrate desiccated regions of tissue, thereby aiding in the delivery of RF energy and expansion of the lesion site.

In one embodiment, the system 100 may include first and second probes 200 and may be operated in a bipolar mode. In such embodiments, electrical energy is delivered to the first and second probes 200 and this energy is preferentially concentrated therebetween through a region of tissue to be treated. The region of tissue to be treated is thus heated by the energy concentrated between first and second probes 200. In other embodiments, the first and second probes 200 may be operated in a monopolar mode, in which case a grounding pad 300 is required on the surface of a body 10 of a patient, as is known in the art. Any combination of bipolar and monopolar procedures may also be used. It should also be understood that the system may include more than two probes 200. For example, in some embodiments, three probes 200 may be used and the probes 200 may be operated in a triphasic mode, whereby the phase of the current being supplied differs for each probe 200.

In further embodiments, the system may also be configured to control one or more of the flow of current between electrically conductive components and the current density around a particular component. For example, a system 100 of the present invention may include three electrically conductive components, including two of similar or identical dimensions, e.g., two probes 200, and a third of a larger dimension, e.g., a grounding electrode 300, sufficient to act as a dispersive electrode. Each of the electrically conductive components should beneficially be operable to transmit energy between a patient's body 10 and a power source 120. Thus, two of the electrically conductive components may be probe assemblies 200 while the third electrically conductive component may function as a grounding pad 300 or dispersive/return electrode. In one embodiment, the dispersive electrode 300 and a first probe 200 are connected to a same electric pole while a second probe is connected to the opposite electric pole. In such a configuration, electrical current may flow between the two probes or between the second probe and the dispersive electrode. To control the current to flow preferentially to either the first probe assembly or the dispersive electrode, a resistance or impedance between one or more of these conductive components (i.e. the first probe and the dispersive electrode) and a current sink (e.g. circuit 'ground') may be varied. In other words, if it would be desirable to have current flow preferentially between the second probe and the dispersive electrode (as in a monopolar configuration), then the resistance or impedance between the first probe and the circuit 'ground' may be increased so that the current will prefer to flow through the dispersive electrode to 'ground' rather than through the first probe (since electrical current preferentially follows a path of least resistance). This may be useful in situations where it would be desirable to increase the current density around the second probe assembly and/or decrease the current density around the first probe. Similarly, if it would be desirable to have current flow preferentially between the second probe and the first probe (as in a bipolar configuration), then the resistance or impedance between the dispersive electrode and 'ground' may be increased so that the current will prefer to flow through the first probe assembly to 'ground' rather than through the dispersive electrode. This would be desirable when a standard bipolar lesion should be formed. Alternatively, it may desirable to have a certain amount of current flow between the second probe and the first probe with the remainder of current flowing from the second probe to the dispersive electrode (a quasi-bipolar configuration). This may be accomplished by varying the impedance between at least one of the first probe assembly and the dispersive electrode, and 'ground', so that more or less current will flow along a desired path. This would allow a user to achieve a specific, desired current density around a probe. Thus, this feature of the present invention may allow a system to be alternated between monopolar configurations, bipolar configurations or quasi-bipolar configurations during a treatment procedure.

Still referring to FIG. 1, the system 100 may include a controller 110 and processor 112 for facilitating communication between the cooling device 130, the suction device 140, and/or the fluid injection device 150, and the generator 120. In this way, feedback control is established between the generator 120 and the cooling device 130, the suction device 140, and/or the fluid injection device 150. The feedback control may include the generator 120, the probe 200 and the suction device 140, and/or the fluid injection device 150, although any feedback between any two devices is within the scope of the present invention. The feedback control may be implemented, for example, in a control module which may be present independent of the generator 120, as shown in FIG. 1, or alternatively which may be a component of the generator 120. In such embodiments, the generator 120 is operable to communicate bi-directionally with the probe 200 as well as with the cooling device 130, suction device 140 and/or fluid injection device 150. In the context of this invention, bi-directional communication refers to the capability of a device to both receive a signal from and send a signal to another device.

As an example, the controller 110 may receive one or more temperature measurements from the probe 200. Based on the temperature measurements, the generator 120 may perform some action, such as modulating the power that is sent to the probe 200. Thus, each probe 200 of the system 100 may be individually controlled based on its respective temperature measurements. For example, power to each probe 200 can be increased when a temperature measurement is low or decreased when a measurement is high. This variation of power may be different for each probe 200. In some cases, the generator 120 may terminate power to one or more probes 200. Thus, the controller 110 may receive a signal (e.g. temperature measurement) from one or more probes 200, determine the appropriate action, and send a signal (e.g. decreased or increased power) via the generator 120 back to the one or more probes. Alternatively, the controller 110 may send a signal to the cooling device 130 to either increase or decrease the degree of cooling being supplied to each probe 200. When using more than one probe 200, the average temperature or a maximum temperature in the temperature sensing elements associated with probe 200 may be used to modulate cooling. In other embodiments, the cooling device 130 may reduce the rate of cooling or disengage depending on the distance between a plurality of probe assemblies 200. The cooling device 130 may also communicate with the controller 110 to alert the controller 110 to one or more possible errors and/or anomalies associated with the cooling device 130. For example, if cooling flow is impeded, the controller 110 may then act on the error signal by at least one of alerting a user, aborting the procedure, and modifying an action.

The present invention is further directed to an adaptive multivariate control system and method for the RF ablation system 100. For instance, the control system can initiate an ablation procedure by controlling energy delivery and/or cooling based on one factor (e.g., power control, temperature control, or impedance control). Meanwhile, one or more sensor(s) in the probe 200 and/or controller 110 continuously monitor a plurality of characteristics of the RF ablation procedure, including but not limited to tissue temperature at the target ablation site, energy (voltage) delivered, current, impedance, stimulation time, cooling characteristics (e.g., flow rate of cooling fluid) for cooled probes, or a combination thereof. For instance, one combined set of characteristics that may be monitored is the rate of change of impedance over time during RF ablation. The control system can then switch to follow and control energy delivery based on a different one of the characteristics in order to further develop the lesion. The decision to switch between control factors is informed by continuously monitoring each of the characteristics and the combination thereof. The control system can autonomously make the decision to switch between control factors using algorithms 115 stored on the memory device 114. Additionally or alternatively, the decision to switch between control factors can be directed by the user, e.g., via the user input 116.

In an RF ablation procedure, the radiofrequency probe system 100 and probe(s) 200 for use to treat tissue of a patient's body. For example, preparing the radiofrequency system 100 and probe(s) 200 to treat the tissue may include determining a desired lesion size (or volume) and/or a rate of power delivery initially required to treat the tissue. Then, the probe(s) 200 are inserted into and positioned in the patient's body. More specifically, the elongate member(s) 210 of each probe 200, each having an active energy delivery distal tip 218, are inserted into the patient's body, and the active distal tip 218 of each elongate member(s) 210 is routed to the target tissue 20 of the patient's body 10. For example, in one embodiment, with a patient lying on a radiolucent table, fluoroscopic guidance may be used to percutaneously insert an introducer with a stylet to access the posterior of an intervertebral disc. In addition to fluoroscopy, other aids, including but not limited to impedance monitoring and tactile feedback, may be used to assist a user to position the introducer or probe(s) 200 within the patient's body. The use of impedance monitoring has been described herein, whereby a user may distinguish between tissues by monitoring impedance as a device is inserted into the patient's body. With respect to tactile feedback, different tissues may offer different amounts of physical resistance to an insertional force. This allows a user to distinguish between different tissues by feeling the force required to insert a device through a given tissue. A second introducer with a stylet may then be placed contralateral to the first introducer in the same manner, and the stylets are removed. Thus, the probe(s) 200 can be inserted into each of the two introducers placing the electrodes 246 in the tissue at suitable distances, such as from about 1 mm to about 55 mm.

The RF ablation procedure further includes coupling a power source (e.g. the generator 120) to the probe(s) 200. Once in place, a stimulating electrical signal may be emitted from either of the electrodes 246 to a dispersive electrode or to the other electrode 246. When the ablation procedure is used to treat chronic pain, e.g., in a disc in the spine, this signal may be used to stimulate sensory nerves where replication of symptomatic pain would verify that the disc is pain-causing. In addition, since the probe(s) 200 may be connected to the RF generator 120 as well as a cooling device 130, the RF ablation procedure may include simultaneously activating the cooling device 130 and delivering energy from the RF generator 120 to the tissue through the elongate members 210. In other words, radiofrequency energy is delivered to the electrodes 242 and the power is altered according to the temperature measured by temperature sensing element 247 in the tip of the electrodes 242 such that a desired temperature is reached between the distal tip regions 218 of the two probes 200.

During the procedure, a treatment protocol such as the cooling supplied to the probe(s) 200 and/or the power transmitted to the probe(s) 200 may be adjusted and/or controlled to maintain a desirable treatment area shape, size and uniformity. More specifically, the RF ablation procedure includes actively controlling energy delivered to the tissue, such as by controlling both an amount of energy delivered through the electrodes 242 and individually controlling the cooling device 130, suction device 150, and/or fluid injection device 140, if present. In further embodiments, the generator 120 may control the energy delivered to the tissue based on the measured temperature measured by the temperature sensing element(s) 247 and/or impedance sensors.

Figure 8:
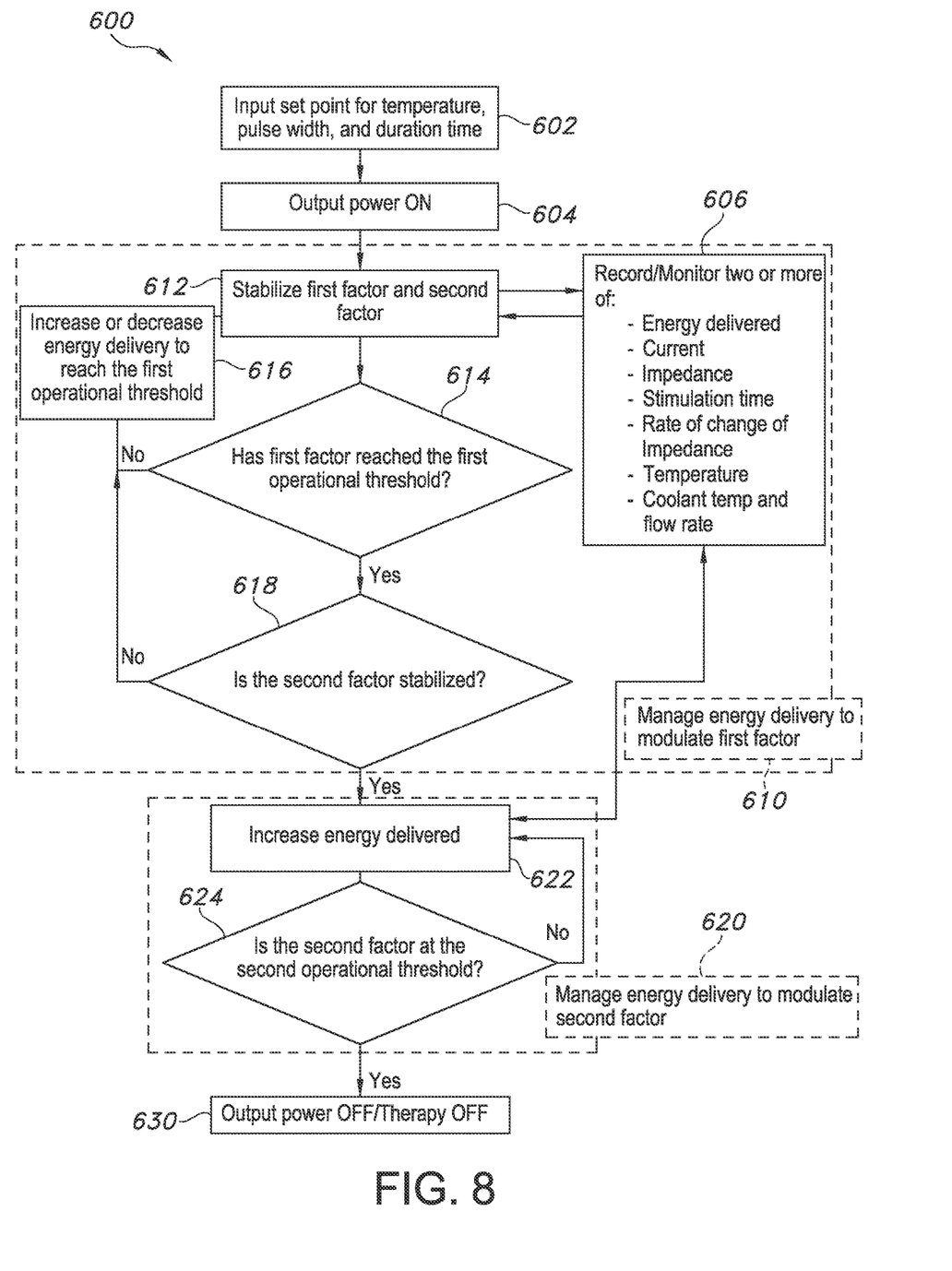
FIG. 8 illustrates a system diagram of a pump assembly according to an embodiment of the present invention.

More specifically, as shown in FIG. 8, a block diagram of one embodiment of a treatment procedure method 600 using an adaptive multivariate control method to control the radiofrequency ablation procedure according to the present invention is shown. For example, in the method 600, two variables are used to control the procedure. the RF ablation procedure may begin with energy delivery to achieve a set temperature. Then, the control system may shift to control the energy delivery based on tissue impedance rise or spike (i.e., rate of change of impedance). For instance, the control system may shift to controlling based on rate of change of impedance after the set temperature has been reached. All of the other characteristics of the RF ablation treatment are continuously recorded and monitored as shown at 606 so that the control system can take real-time action to increase, decrease, or turn off the energy delivery through the probe 200.

As shown at 602, initial settings (i.e., a set point) for temperature, pulse width of energy delivered, and duration time are entered, e.g., via the user input 116. The operational thresholds for the first factor, e.g., temperature, and the second factor, e.g., impedance, may be input during step 602 as well. As shown at 604, output power of the generator 120 for energy delivery is initiated to deliver energy through the probe(s) 200. As shown at 606, two or more factors or characteristics related to the ablation procedure are continuously monitored and recorded. These factors may include, but are not limited to, one or more of: energy delivered, power (voltage), current, tissue impedance, stimulation time, rate of change of tissue impedance, tissue temperature, coolant temperature, and coolant flow rate. In the first treatment phase 610 of the method 600, the controller 110 controls the energy delivery via the probe(s) 200 to modulate a first factor, e.g., temperature. At 612, the first and second factors, e.g., tissue temperature and tissue impedance, are measured to determine whether the first and second factors have stabilized. Then, at 614, the measurement of the first factor is compared to the first operational threshold set at 602 to determine if the first operational threshold has been reached. If the first operational threshold is not reached, then the energy delivery is increased or decreased, as shown at 616. The first treatment phase 610 continues until the first operational threshold has been reached. Then, at 618, the measurement of the second factor, e.g., impedance, is compared to the second operational factor to determine if the second operational factor is stabilized, i.e., is not changing. If so, then the control method proceeds to the second treatment phase 620 in which the energy delivery is managed to modulate the second factor, e.g., impedance.

In the second treatment phase 620, the second factor, e.g., impedance, is monitored and compared to the second operational threshold as shown at 624. If the second operational threshold has not been reached, the energy delivered is increased at 622. The second treatment phase 620 continues until the second operational threshold, e.g., a specific impedance value or rate of change of impedance, has been reached. Finally, at 630, the treatment ends and the output power is turned off.

Although an embodiment of the method 600 in which temperature and impedance are used in the adaptive multivariate control of a radiofrequency ablation procedure is described above, it is to be understood that the adaptive multivariate control contemplated by the present invention may implement controls based on two or more of energy delivered, power (voltage), current, impedance, stimulation time, rate of change of impedance, temperature, coolant temperature, and coolant flow rate, or combinations thereof.

Moreover, the method 600 may further include developing and training a tissue lesion deep learning network, i.e., using artificial intelligence, to automatically adapt the delivery of energy for tissue ablation to a changing tissue environment. For instance, in several embodiments, the system 100 is configured to train the deep learning network to automatically learn the method steps relating to multivariate control and operation of the probe 200 based on a changing tissue environment. In one embodiment, the deep learning network may be trained once offline. More specifically, the processor 112 inputs the collected data into the deep learning network, which is configured to learn the steps relating to multivariate control and operation of the probe 200 based on a changing tissue environment during lesion formation. Further, the treatment patterns may be input into the deep learning network. As used herein, the deep learning network may include one or more deep convolutional neural networks (CNNs), one or more recurrent neural networks, or any other suitable neural network configurations. In machine learning, deep convolutional neural networks generally refer to a type of feed-forward artificial neural network in which the connectivity pattern between its neurons is inspired by the organization of the animal visual cortex, whose individual neurons are arranged in such a way that they respond to overlapping regions tiling the visual field. In contrast, recurrent neural networks (RNNs) generally refer to a class of artificial neural networks where connections between units form a directed cycle. Such connections create an internal state of the network which allows the network to exhibit dynamic temporal behavior. Unlike feed-forward neural networks (such as convolutional neural networks), RNNs can use their internal memory to process arbitrary sequences of inputs. As such, RNNs can extract the correlation between the changing tissue environment, lesion development and the energy delivered by the RF probe in order to better identify and predict changes in the tissue environment and treatment patterns for controlling RF energy delivery in response to the changing tissue environment in real time.

The system may also be configured to determine an error between the controlled RF energy delivery and the sensed tissue environment. In such embodiments, the method may further include optimizing the deep learning network based on the error. More specifically, in certain embodiments, the processor(s) 112 may be configured to optimize a cost function to minimize the error. For example, in one embodiment, the step of optimizing the cost function to minimize the error may include utilizing a stochastic approximation, such as a stochastic gradient descent (SGD) algorithm, that iteratively processes portions of the collected data and adjusts one or more parameters of the deep neural network based on the error. As used herein, a stochastic gradient descent generally refers to a stochastic approximation of the gradient descent optimization method for minimizing an objective function that is written as a sum of differentiable functions. More specifically, in one embodiment, the processor(s) 112 may be configured to implement supervised learning to minimize the error. As used herein, "supervised learning" generally refers to the machine learning task of inferring a function from labeled training data.

Once the deep neural network is trained, the controller 110 of the system is configured to control the RF energy delivery based on the deep learning network. More specifically, the collected data from the system is used an input to the deep learning network that controls the RF energy delivery.

Example

Multiple trials of radiofrequency (500 kHz) electrical stimulation were delivered to chicken breast (in-vitro) held at 37° C., to compare lesion sizes created by the adaptive multivariate-controlled ablation paradigm of the present invention with conventional, temperature-controlled of radiofrequency ablation. All trials were delivered through a standard ablation probe (PMP-22-100, Avanos Medical, Alpharetta GA) and a manually controlled generator (Radionics, Burlington MA) into a piece of raw chicken breast tissue. Three radiofrequency stimulation methods were tested, and three trials were performed for each stimulation method. The radiofrequency stimulation methods were as follows:

(1) Adaptive multivariate stimulation. Radiofrequency stimulation was delivered via the standard radiofrequency ablation probe controlled by temperature for the first 60 seconds, then controlled by tissue impedance afterwards. Specifically, electrical power was increased to reach a set-temperature of 80° C. for 60 seconds, and then power was increased again until impedance spiked to levels above 10000Ω. The impedance spike typically occurred a few seconds short of 60 seconds, making the entire trial length about 117-119 seconds.

(2) Temperature control at 95° C. for 120 seconds ('high temperature' radiofrequency ablation).

(3) Temperature control at 80° C. for 120 seconds (standard radiofrequency ablation).

It is known that ablative temperatures above 100° C. causes tissue charring that will significantly limit lesion size. Accordingly, the High-temperature group marks the practical limit of the lesion size created with a temperature-controlled paradigm and our instrumentation.

The lesions formed in the tissue by the radiofrequency ablation were evaluated as follows: The long (b) and short (a) semi-axes of the lesions were measured in 2 dimensions. All lesions resembled a prolate spheroid in shape (i.e., the shape of an American football). The volume of each lesion was calculated accordingly as a prolate spheroid:

$$\text{volume} = \left(\frac{4}{3}\right) * \pi b^2 a.$$

TABLE 1

| Lesioning Method | Length A (mm) | Length B (mm) | Lesion Volume (mm³) | Volumetric % change compared to Standard |
|---|---|---|---|---|
| Adaptive Control (80° C. for 60 s, Z ~60 s) | 6.75 | 4.00 | 452.16 | 278.11 |
| | 7.00 | 4.00 | 468.91 | |
| | 7.00 | 3.75 | 412.13 | |
| High Temp. (95° C., 120 s) | 5.25 | 3.50 | 269.26 | 185.67 |
| | 6.50 | 3.25 | 287.44 | |
| | 6.50 | 3.50 | 333.36 | |
| Standard (80° C., 120 s) | 5.25 | 3.00 | 197.82 | |
| | 5.00 | 2.00 | 83.73 | |
| | 5.25 | 3.00 | 197.82 | |

As shown in Table 1 above, the lesions formed by the adaptive multivariate stimulation of the present invention were on average 278% larger in volume than those made by the standard (80° C.) temperature-controlled ablation, and 150% larger than those made by the high-temperature (95° C.) ablation (Table 1).

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A radiofrequency (RF) ablation system for performing an RF ablation procedure, the RF ablation system comprising:
   an energy source for delivering energy to a target site of a patient's body;
   an energy delivery device electrically coupled to the energy source;
   two or more sensors for measuring at least two factors, respectively, related to the RF ablation procedure; and
   at least one processor configured to perform a plurality of operations, the plurality of operations comprising:
     operating the energy delivery device to deliver energy to create a lesion at the target site within the patient based on a first factor of the at least two factors;
     while delivering energy to the target site, monitoring the at least two factors related to the RF ablation procedure based on measurements from the two or more sensors;
     determining whether the first factor of the at least two factors has reached a first operating threshold for the energy delivery device responsive to a determination that measurements of the first factor have stabilized;
     increasing or decreasing the energy delivered to the target site responsive to a determination that the first factor has not reached the first operating threshold;
     switching control of the energy delivery device from the first factor to a second factor of the at least two factors once the first operating threshold has been met by the first factor to further develop the lesion at the target site within the patient;
     determining whether the second factor of the at least two factors has reached a second operating threshold for the energy delivery device responsive to a determination that measurements of the second factor have stabilized;
     increasing the energy delivered to the target site responsive to a determination that the second factor has not reached the second operating threshold; and
     terminating the delivery of energy to the target site once the second operating threshold has been met by the second factor.

2. The system of claim 1, wherein the at least two factors comprises at least two of: power, current, voltage, impedance, temperature of tissue at the target site, temperature of a coolant associated with a cooling device for the RF ablation procedure, duration (time) of stimulation, rate of current change, rate of voltage change, rate of power change, rate of temperature change of the tissue at the target site, rate of temperature change of the coolant, pressure at the target site, gas formation at the target site, rate of change of gas formation at the target site, or a combination thereof.

3. The system of claim 2, wherein one of the at least two factors is rate of change of tissue impedance.

4. The system of claim 1, wherein the system is configured to continuously monitor and record the at least two factors.

5. The system of claim 1, wherein the first factor is a tissue temperature at the target site.

6. The system of claim 1, wherein the second factor is tissue impedance or rate of change of tissue impedance at the target site within the patient.

7. The system of claim 1, wherein the system is configured to:
   determine a third operating threshold for the energy delivery device based, at least in part, on a third factor; and
   switch control of the energy delivery device from the first operating threshold or the second operating threshold to the third operating threshold to further develop the lesion at the target site.

8. The system of claim 1, wherein at least one sensor of the two or more sensors is configured to measure a respective factor related to the RF ablation procedure at the target site.

9. The system of claim 1, wherein the energy delivery device comprises an RF probe comprising:
   an elongate member having a proximal end and a distal end, the distal end comprising an electrically and thermally-conductive energy delivery device for delivering one of electrical and RF energy to a patient's body, the RF probe having at least one electrode and an electrically and thermally-conductive portion having a temperature sensing element; and
   one or more ablation enhancing features comprising: a cooling device extending within the elongate member, a suction mechanism having a suction path, a fluid injection mechanism having a fluid path, and/or a directional energy delivery mechanism.

10. The system of claim 9, wherein the two or more sensors comprises, at least, a thermocouple positioned on the RF probe.

11. The system of claim 1, wherein control of the energy delivery device is switched from the first factor to the second factor responsive further to a determination at that the measurements of the second factor have stabilized.

12. The system of claim 1, the plurality of operations further comprising ending the RF ablation procedure by terminating the delivery of output power to the one or more energy delivery devices once the second operating threshold has been met.

13. A method for performing a radiofrequency (RF) ablation procedure with an RF probe, the method comprising:
- operating the RF probe to deliver energy to create a lesion at a target site within a patient based on a first operational factor related to an ablation procedure performed with the RF probe;
- while delivering energy to the target site, monitoring the first operational factor and a second operational factor related to the ablation procedure that is different from the first operational factor, wherein the first and second operational factors are monitored using measurements from sensors configured to measure the first operational factor and the second operational factor, respectively;
- determining whether the first operational factor has reached a first operating threshold for the RF probe responsive to a determination that measurements of the first operational factor have stabilized;
- increasing or decreasing the energy delivered by the RF probe responsive to a determination that the first operational factor has not reached the first operating threshold;
- switching control of the RF probe from the first operational factor to the second operational factor once the first operating threshold has been met by the first operational factor to further develop the lesion at the target site within the patient;
- determining whether the second operational factor has reached a second operating threshold responsive to a determination that measurements of the second operational factor have stabilized;
- increasing the energy delivered to the target site responsive to a determination that the second operational factor has not reached the second operating threshold; and
- terminating the delivery of energy to the target site once the second operating threshold has been met by the second operational factor.

14. The method of claim 13, further comprising steps of:
- collecting data relating to operation of the RF probe during use;
- inputting the collected data into a deep learning network to train the deep learning network to control the energy delivered to the target site based on the first operational factor and the second operational factor; and
- controlling the RF probe based on the deep learning network.

* * * * *